US00PP09643P

United States Patent [19]

Escande

[11] Patent Number: Plant 9,643

[45] Date of Patent: Sep. 17, 1996

[54] NECTARINE TREE 'CRYSTAL BELLE'

[76] Inventor: Jean L. Escande, 47500 Fumel, Sainte-Vite, France

[21] Appl. No.: 510,262

[22] Filed: Aug. 2, 1995

[51] Int. Cl.[6] ..... A01H 5/00

[52] U.S. Cl. ..... Plt./40.1

[58] Field of Search ..... Plt./40.1

*Primary Examiner*—James R. Feyrer

*Attorney, Agent, or Firm*—Wells, St. John, Roberts, Gregory & Matkin, P.S.

[57] ABSTRACT

A new and distinct variety of nectarine tree which has a harvesting date which is earlier than that of the Arctic Glo nectarine tree [U.S. Plant Pat. No. 7,884], which matures in the same season, but which is distinguished therefrom and characterized principally as to novelty by producing fruit which have a semi-freestone nature, firm flesh texture, and an attractive skin color at commercial maturity.

1 Drawing Sheet

BACKGROUND OF THE NEW VARIETY

The present invention relates to a new and distinct variety of nectarine tree which is hereinafter denominated varietarily as "Crystal Belle" and more particularly to such a nectarine tree which bears an attractively colored semi-freestone fruit which has a firm, white colored flesh, and which is mature for harvesting and shipment in early June. The present variety of nectarine tree is somewhat similar in its date of harvesting with that of the Arctic Glo nectarine tree [U.S. Pat. No. 7,884], which is ripe for harvesting and shipment approximately June 9 under the ecological conditions prevailing in the San Joaquin Valley of Central California, but which is distinguishable therefrom by being ripe for harvesting and shipment as early as June 1 under the same ecological conditions.

ORIGIN AND ASEXUAL REPRODUCTION OF THE NEW VARIETY

It has long been recognized that an important factor contributing to the success of any variety of nectarine tree bearing fruit for delivery to the fresh market is the propensity for the fruit produced by these trees to be attractive in appearance. Another important factor is that the variety bear fruit at a time when other fruit of the same desirable qualities is not normally available for commercial purchase.

As noted earlier, the present variety of nectarine tree produces semi-freestone fruit in contrast to the fruit produced by the Arctic Glo nectarine tree which produces fruit which are clingstone by nature. Further, in relative comparison to the fruit produced by the Arctic Glo nectarine tree, the flavor of the fruit produced by the Crystal Belle nectarine tree is moderately acidic and sweet and further has a good balance, as opposed to the flavor of the fruit of the Arctic Glo nectarine tree which is considered to be subacid and mild.

The new and distinct variety of nectarine tree hereof is a hybrid nectarine tree resulting from the cross pollination of one of the inventor's stock nectarine trees, which is identified by the alpha-numeric designator 1S ¾ and which is of unknown parentage. This stock tree was cross pollinated with the Snow-Queen nectarine tree.

Cross pollination of the trees, identified above, took place at the inventor's farm which is located near St. Vite, France. A selection from this cross pollination was germinated and several buds were removed from the original offspring and grafted into commercial rootstock which was then growing within the cultivated area of this same farm. Over the last several years, the fruit and grafted trees were compared and contrasted with that of the original cross pollinated offspring and it has been subsequently determined that this asexual propagation resulted in a nectarine tree being produced which possesses the same distinctive characteristics as the originally selected offspring resulting from the aforementioned cross pollination. As compared with the original parents, the present variety of nectarine tree produces fruit which are larger in size and more highly colored than those of the original parents.

SUMMARY OF THE NEW VARIETY

The new variety of nectarine tree described herein is characterized principally as to novelty by being ripe for harvesting and shipment on or about June 1 under the ecological conditions prevailing in the San Joaquin Valley of Central California. The variety is further distinguished from other known varieties by producing fruit which have a substantially ovate form in its lateral aspect and an oval form in its apical aspect. Additionally, the highly colored exterior appearance of the variety distinguishes it from that of the Arctic Glo nectarine tree which is less highly colored and which is ripe for harvesting and shipment some seven days later. Lastly, the present variety of nectarine tree produces semi-clingstone fruit as compared to the Arctic Glo nectarine tree which produces a clingstone fruit.

BRIEF DESCRIPTION OF THE DRAWING

The accompanying drawing is a color photograph of five mature fruit, one of which has been divided in the axial plane to show the flesh, and stone characteristics, together with a twig bearing typical leaves which display the coloration of the top and bottom surfaces thereof, along with a representative stone, all of the subject variety.

DETAILED DESCRIPTION

Referring more specifically to the pomological details of this new and distinct variety of nectarine trees, the following has been observed under the ecological conditions prevailing at the applicant's licensee's orchard which is located near Traver, Calif. All major color code designations are made by a reference to the "*Dictionary of Color*" by Maerz & Paul, First Edition, 1930. Common color names are also employed occasionally.

Tree:

*Size.*—Generally — Medium. Test trees of the present variety were propagated by dormant budding in 1990 on seedling peach rootstock. In July of 1994, these same test trees had attained a height of approximately 11.5 to 12.5 feet, including 3.5 to 4.5 feet of new growth. The subject test trees were trained in a two leader palmette system which had a spread of approximately 9 feet by 6 feet in its two respective dimensions.

*Form.*—Generally — The tree form is considered upright to upright spreading. The final form of the tree will be determined by pruning practices. As noted above, the test trees are trained in a two-leader palmette system with a spread of approximately 9 feet by 6 feet in its two respective dimensions.

*Productivity.*—Productive.

*Vigor.*—Vigorous, and hardy under typical central San Joaquin Valley climatic conditions.

*Regularitive bearing.*—Regular.

Trunk:

*Size.*—Generally — Average in view of the age of the tree.

*Trunk diameter.*—Approximately 76 to 89 millimeters when measured at a point immediately above the rootstock union.

*Surface texture.*—Considered moderately rough with light scarfskin being evident.

*Lenticels.*—Numbers — Numerous medium sized bark lenticels are present throughout the bark surface.

*Lenticel shape.*—Oval, and having dimensions of approximately 3 to 7 millimeters in width, and approximately 1 to 2 millimeters in height.

*Bark color.*—Brown — Grey [6-A-10].

Branches:

*Size.*—Generally — average in thickness.

*Surface texture.*—Variable, from relatively smooth to moderately rough.

*Color.*—Mature shoots — Shoots that are at least two years old are considered medium brown [7-A-11].

*Color of current season shoots.*—Pale green, [17-J-6]. Further, portions of the new shoots which are exposed to direct sunlight have a rose-red blush [4-J-3].

*Internode length.*—Current season fruiting wood — Approximately 27 to 39 millimeters.

*Shoot tip color.*—Bright green-yellow [19-L-5].

Leaves:

*Size.*—Generally. Medium to large.

*Average length.*—All leaves were measured from vigorous, upright, current season's growth. These leaves have a length of about 19.6 centimeters to about 21.6 centimeters including the leaf petiole.

*Average width.*—Approximately 4.9 centimeters to about 6.5 centimeters.

*Leaf thickness.*—This characteristic appears slightly thicker than average.

*Leaf form.*—Generally — Lanceolate.

*Leaf apices.*—Generally — Acuminate. The leaf tip often appears slightly curled, and twisted sideways.

*Surface texture.*—Upper surface — Glabrous.

*Marginal form.*—Crenate. The leaves have rather large, low and regular crenations. As a general matter, the leaf margins are moderately to substantially undulate.

*Leaf petiole.*—Size — Medium to large, as compared with other known varieties.

*Length.*—Approximately 10 to 15 millimeters.

*Thickness.*—Approximately 2 to 3 millimeters.

*Color.*—Pale green [19-J-5]. A darker green color appears within the petiolar groove [21-K-6].

*Leaf color.*—Top surface — dark green [23-L-4].

*Lower leaf surface.*—A lighter, grey-green [22-K-4].

*Color — mid vein.*—On the lower leaf surface, this color is a pale green-yellow [17-I-4].

*Leaf glands.*—Size — Variable from quite large to quite small.

*Gland form.*—Predominantly reniform. Occasionally stalked glands may be found and these may be globose in form.

*Gland number.*—Variable, from two to as many as seven may be found. As a general matter, two to four glands normally appear on the petiole and one pair is positioned in close proximity to the base of the leaf margin. Still further, the petiole glands are strongly reniform unless they appear in the stalked form, in which case, the stalked form of the glands can have a reniform or globose shape. Additonally, one or two small, reniform shaped glands can be located along the base of the leaf margin.

*Gland position.*—Most frequently alternate.

*Gland color.*—Bright Green, [20-L-3] and becoming darker with advancing senescence.

*Leaf stipule size.*—Small.

*Leaf stipule length.*—Approximately 8 to 11 millimeters.

*Leaf stipule form.*—Linear lanceolate.

*Leaf stipule marginal form.*—Serrate.

*Leaf stipule color.*—Bright and shiny green when young, [20-I-4], and becoming darker with advancing senescence. The leaf stipules are considered to be early deciduous.

Flowers:

*Blooming time.*—Generally — Average in comparison to other common commercial nectarine varieties which are grown in the San Joaquin Valley of Central California. In 1994, the date of full bloom was Mar. 3, 1994, at the test plot which is located near Traver, Calif.

*Floral buds.*—Size — Medium.

*Shape.*—Conic. The floral buds are borne relatively free from the bearing stem. The flower buds are considered hardy under normal Central San Joaquin Valley climatic conditions.

*Bud scale color.*—Brown — grey [15-A-8].

*Bud scale surface texture.*—Very Pubescent. The pubescence is a dense, dark grey. This color is not distinctive, however.

*Flower size.*—Generally — Large and considered of the showy type.

*Flower diameter.*—The flower, when fully opened, is variable, from 46 to 56 millimeters.

*Bloom quantity.*—Abundant.

*Flowers produced per node.*—Variable, from one to two, most often, two.

*Petal size.*—Generally — Large.

*Petal length.*—Approximately 23 to 27 millimeters.

*Petal width.*—Approximately 22 to 26 millimeters.

*Petal form.*—Broadly Ovate.

*Petal number.*—Five.

*Petal color.*—Light pink, [1-D-1].

*Color — mature petals.*—Dark Pink [1-F-1]. The base of the petal and petal claw becomes a dark rose color [1-I-4] with advancing senescence.

*Petal claw — form.*—Generally — Considered tapering and truncate. Further, the claw appears relatively broad.

*Petal claw width.*—Approximately, 1.5 to 2 millimeters.

*Petal claw length.*—Approximately 1 millimeter.

*Petal claw surface texture.*—Moderately veined.

*Petal margins — form.*—Undulate and often cupped in an inward direction.

*Petal apex — shape.*—Domed.

*Flower pedicle — length.*—Approximately 2.5 to 3 millimeters.

*Pedicle thickness.*—Approximately 1.5 to 2 millimeters.

*Pedicle color.*—Bright green [17-L-7].

*Pedicle surface texture.*—Glabrous.

*Floral nectaries.*—Color — Greenish — yellow [19-J-1]. This color darkens with advancing senescence.

*Calyx — surface texture.*—The surface texture is glabrous and rugose.

*Calyx color.*—As a general matter, it is normally maroon [7-H-3] and further has some green tones which appear basally [17-L-7].

*Sepal — surface texture.*—Pubescent. The pubescence appears along the margin and is usually of medium length, and is greyish-white in color.

*Sepal size.*—Moderately large and having a broadly ovate form.

*Sepal color.*—Maroon [7-J-7].

*Anthers — size.*—Moderately large.

*Anther color.*—Normally deep red, dorsally [5-L-10]; and a buff color, ventrally, [11-H-3]. Further, the anthers may have a marginal edge which has a red color [5-L-10].

*Pollen production.*—Abundant.

*Pollen color.*—Yellow [9-L-3].

*Stamens — length.*—Variable, with the longest stamens having a length dimension of approximately 12 to 18 millimeters. The stamens are normally longer than the pistil.

*Filament color.*—White, [1-A-1] and occasionally light pink [1-B-1]. The filament color darkens with advancing senescence and will appear rose colored [2-I-4].

*Pistil — length.*—Approximately 17 to 19 millimeters including the ovary.

*Pistil surface texture.*—Glabrous.

*Pistil color.*—Pale green — yellow [17-K-2]. With advancing senescence the pistil becomes reddish colored near the stigma end. This color is not particularly distinctive, however.

Fruit:

*Maturity when described.*—Ripe for commercial harvesting and shipment approximate 1 June through 11 June under the ecological conditions prevailing in the San Joaquin Valley of Central California.

*Fruit size.*—Generally — Average in view of the early season of maturity.

*Cheek diameter.*—Approximately 54 to 62 millimeters.

*Suture diameter.*—Approximately 54 to 60 millimeters.

*Axial diameter.*—Approximately 57 to 65 millimeters.

*Uniformity.*—Uniform.

*Fruit form.*—Generally — Variable in its lateral aspect. However, it appears most often ovate. Further, the fruit in its apical aspect is also somewhat variable although it normally appears oval and further has a slightly protruding suture. The fruit shape is considered asymmetrical.

*Fruit suture.*—Generally — The suture appears as a relatively thin line which extends from the base to the apex.

*Fruit suture width.*—Approximately 1 to 2.5 millimeters.

*Fruit suture coloration.*—Variable. At times, the suture has a dark garnet-red color [8-L-6], although occasionally it may appear a lighter red color [6-L-4]. These colors normally blend in with the surrounding blush coloration. At other times, the suture may appear as a lighter color than the surrounding blush color. This color may appear as a medium red [3-L-9], to a pink-red color [2-G-9], with many shade variations therebetween. As a general matter, a moderate amount of red streaking is present in the vicinity of the suture area. In this regard, the streaking ranges in color from dark red [7-J-6], to a lighter red [5-K-9].

*Ventral surface — shape.*—Somewhat uneven and at times appears slightly protruding. The ventral surface is moderately lipped on one side.

*Stem cavity — size.*—Medium.

*Stem cavity width.*—Approximately 21 to 26 millimeters.

*Stem cavity length.*—Approximately 25 to 27 millimeters.

*Stem cavity shape.*—Oval.

*Stem cavity depth.*—Approximately 9 to 11 millimeters.

*Stem well — color.*—Cream — Green [18-D-2].

*Fruit base — form.*—Slightly truncate.

*Base angle.*—Variable, but normally it appears at right angles to the fruit axis.

*Fruit apex shape.*—Slightly domed and having a small dentate pistil point.

*Pistil point — shape.*—Variable with both apical and oblique forms appearing.

*Fruit stem — length.*—Approximately 7 to 9 millimeters.

*Fruit stem thickness.*—Approximately 3 to about 4.5 millimeters.

*Fruit stem color.*—Olive green [13-J-1] and occasionally brown-green [13-I-3].

*Skin color.*—Generally — Variable. Approximately 85% to 95% of the surface color of the skin has a red blush. This blush color appears in a washed pattern with occasional striping. This occurs most commonly basally. As a general matter, the darkest areas of the fruit surface possess a deep garnet-red color [7-J-6]. The lightest blush areas have a pink-red color [5-F-9] with many shade variations therebetween. Considerable russetting may be evident. This russetting can be dense, and may include light colored speckling. This is normally most prevalent over the apical end of the fruit and occasionally laterally.

*Ground color.*—This color is variable and ranges from approximately 5% to about 15% of the fruit surface. Normally, the ground color appears basally or where foliage has covered the fruit surface. The ground color is considered to be cream [9-D-1] and occasionally cream — green [17-H-2].

*Flesh color.*—Generally — White throughout [1-A-1]. This color appears from the skin surface to the area immediately next to the stone.

*Color — stone cavity.*—Cream colored [17-F-1]. Occasionally, some red flecking may occur in the flesh. The color of the red flecking is most closely similar to the color 1-K-7. If red flecking is evident, it is normally located along the ventral suture area and is further more likely to occur during a later stages of maturity.

*Flesh texture.*—Generally — Firm and fine textured.

*Ripening.*—Generally — The fruit appears to ripen first at the apex and then along the ventral surface.

*Flavor.*—Generally — Moderately acidic and sweet. Overall the fruit is considered well-balanced and has a rich flavor.

*Aroma.*—Moderate and very pleasant.

*Eating quality.*—Considered very good in view of the early season of maturity.

Stone:

*Generally.*—Semi-freestone and occasionally freestone at commercial maturity. As a general matter, the stone is held tightly in the stone cavity with no air space being evident between the stone and surrounding flesh. The stone will normally break free cleanly from the flesh at the more advanced stages of maturity.

*Stone size.*—Generally — Small.

*Stone length.*—Approximately 32 to 36 millimeters.

*Stone width.*—Approximately 21 to 24 millimeters.

*Stone thickness.*—Approximately 16 to 18 millimeters.

*Fibers — numbers.*—Moderate, and short. These fibers are attached to the stone, and are normally located basally and on the basal surfaces of the ventral suture.

*Stone form.*—Variable, from oval to occasionally ovate.

*Stone base — shape.*—Variable, from rounded to occasionally truncate.

*Base angle.*—Variable. Normally oblique but occasionally at right angles to the stone axis.

*Hilum — size.*—Medium.

*Hilum — form.*—Oval, and it additionally appears heavily eroded.

*Stone apex — shape.*—Acute and having a narrow, sharp tip.

*Stone sides.*—Variable, and normally unequal, but occasionally at times nearly so.

*Stone surface — texture.*—Rough, and coarsely grooved and pitted. As a general matter, the stone surface is most heavily grooved over the apical shoulders and laterally. Further, large oval to round pits are evident and are normally most concentrated in the area from mid-stone to the base, laterally.

*Ventral edge — shape.*—Moderately prominent and having several coalesced wings. The wings are approximately 4 to 6 millimeters in width, and appear at mid-suture. Further, a strong keel may be located at the base of the ventral suture. The keel may protrude a distance of approximately 3 millimeters to approximately 5 millimeters from the body of the stone.

*Dorsal edge.*—Generally — A deep groove normally appears on the dorsal suture and extends from the base to a distance equal to about 75% of the length of the suture edge. The suture groove narrows to a point where it appears as a line which extends over the apical edge. Further, the apical shoulder is normally substantially eroded. Still further, ridges may appear on each side of the suture groove and are usually deeply cross cut with numerous cross grooves.

*Stone color — dry.*—Light tan [11-I-5].

*Tendency to split.*—Not observed. Occasionally, internal splits were evident.

Use: Fresh market for both local and long distance shipping.

Keeping quality: Good.

Shipping quality: Unknown, although the firm and crisp flesh displayed at commercial maturity indicates that the variety should have noteworthy shipping characteristics.

Resistance to disease: No particular susceptibilities were noted.

Although the new variety of nectarine tree possesses the described characteristics as a result of the growing conditions prevailing at the applicant's licensee's ranch which is located near Traver, Calif., in the central part of the San Joaquin Valley of Central California, it is understood that variations of usual magnitude and characteristics incident to changes in growing conditions, fertilization, pruning and pest control are to be expected.

Having thus described my new variety of nectarine tree, what I claim as new and desired to secure by plant Letters Patent is:

1. A new and distinct variety of nectarine tree substantially as illustrated and described and which is somewhat similar to the Arctic Glo nectarine tree [U.S. Plant Pat. No. 7,884] which matures in approximately the same season, but which is distinguishable therefrom, and characterized principally as to novelty by producing fruit which are mature for harvesting and shipment on approximately June 1 through June 11 under the ecological conditions prevailing in the San Joaquin Valley of Central California, and which further has an attractive, bright red exterior coloration, and is semi-freestone, to freestone by nature.

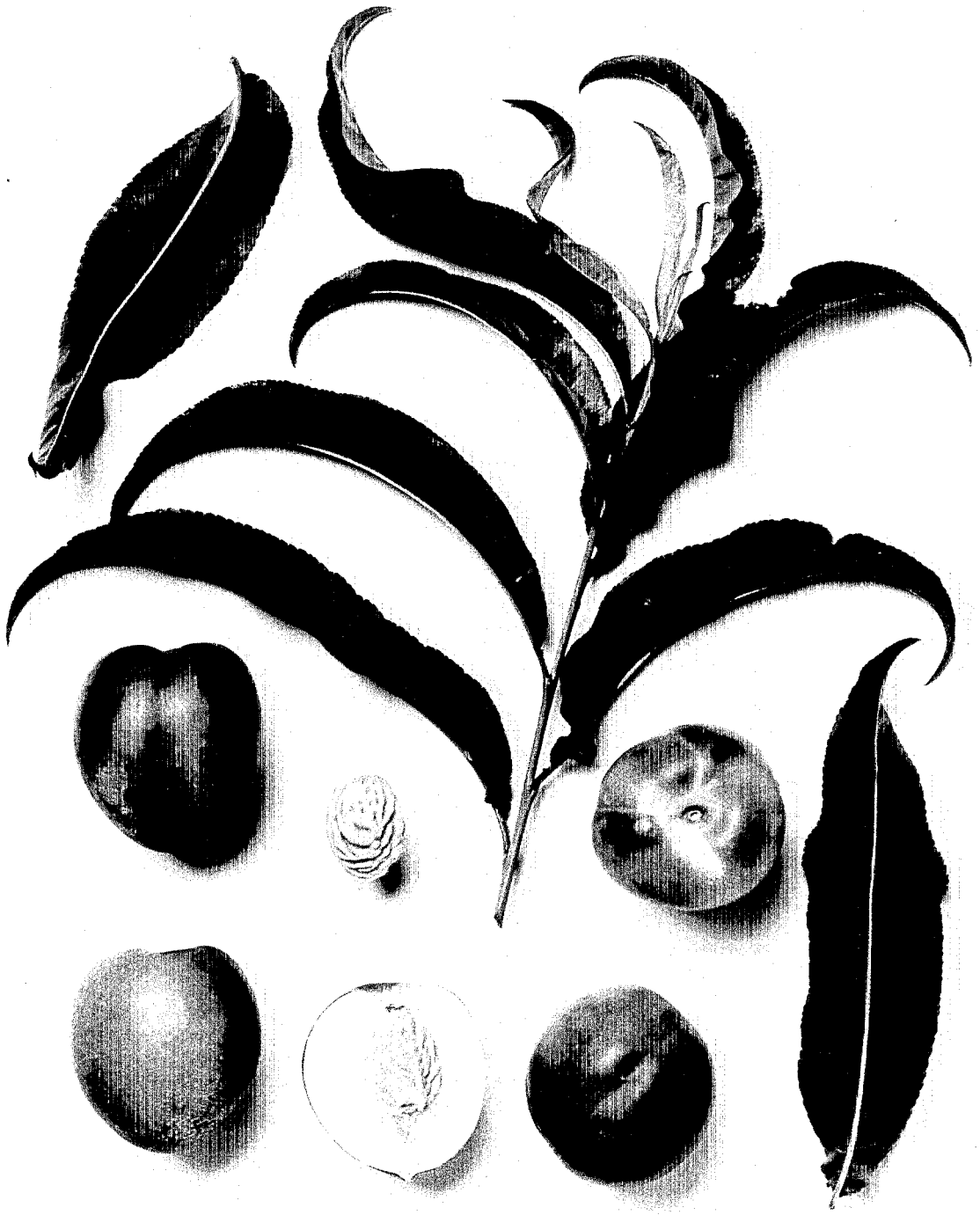

* * * * *